United States Patent [19]

Schulze et al.

[11] Patent Number: 5,439,468
[45] Date of Patent: Aug. 8, 1995

[54] SURGICAL CLIP APPLIER

[75] Inventors: Dale Schulze, Lebanon, Ohio; Dirk Höppner, Hamburg, Germany

[73] Assignee: Ethicon Endo-Surgery, Cincinnati, Ohio

[21] Appl. No.: 226,192

[22] Filed: Apr. 11, 1994

Related U.S. Application Data

[63] Continuation-in-part of Ser. No. 59,147, May 7, 1993.

[30] Foreign Application Priority Data

May 24, 1993 [DE] Germany ............... 43 17 590.2

[51] Int. Cl.⁶ .............................................. A61B 17/04
[52] U.S. Cl. ...................................... 606/143; 227/19; 227/177; 227/179; 227/901
[58] Field of Search ................. 227/175-182, 227/19, 121, 901, 902, 19, 177, 179, 901; 606/142, 143

[56] References Cited

U.S. PATENT DOCUMENTS

| | | | |
|---|---|---|---|
| 4,747,531 | 5/1988 | Brinkerhoff et al. | 227/19 |
| 4,807,628 | 2/1989 | Peters et al. | 227/19 |
| 5,174,487 | 12/1992 | Rothfuss et al. | 227/176 |

FOREIGN PATENT DOCUMENTS 4024106  4/1992  Germany ................ A61B 17/068

Primary Examiner—Gary Jackson
Attorney, Agent, or Firm—Paul A. Coletti

[57] ABSTRACT

The rod system consists of an outer guide tube in which there is arranged an inner sliding sleeve, displaceable coaxially to the outer guide tube, in which are located an elongated support rod fixed relative to the outer guide tube an elongated slide displaceable on the support rod. The holding and shaping mechanism comprised by sliding sleeve, support rod and slide, project from the distal end of the outer guide tube in a manner guaranteeing the holding and shaping function of the clip or staple applying apparatus. After the distal end of the slide, designed as a tip, has struck the anvil, it displaces the sliding sleeve in the same direction beyond the distal end of the support rod and of the slide. The sliding sleeve and the slide return to the starting position in the proximal direction upon release of the actuating lever.

4 Claims, 6 Drawing Sheets

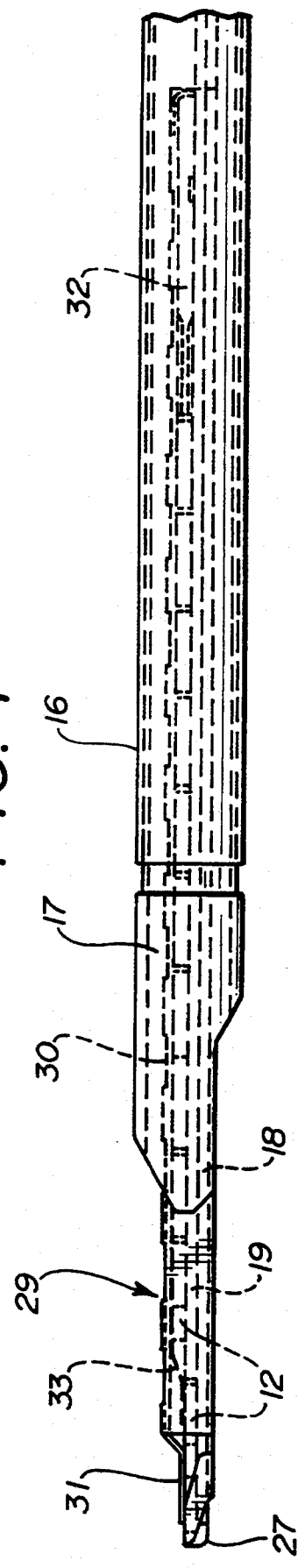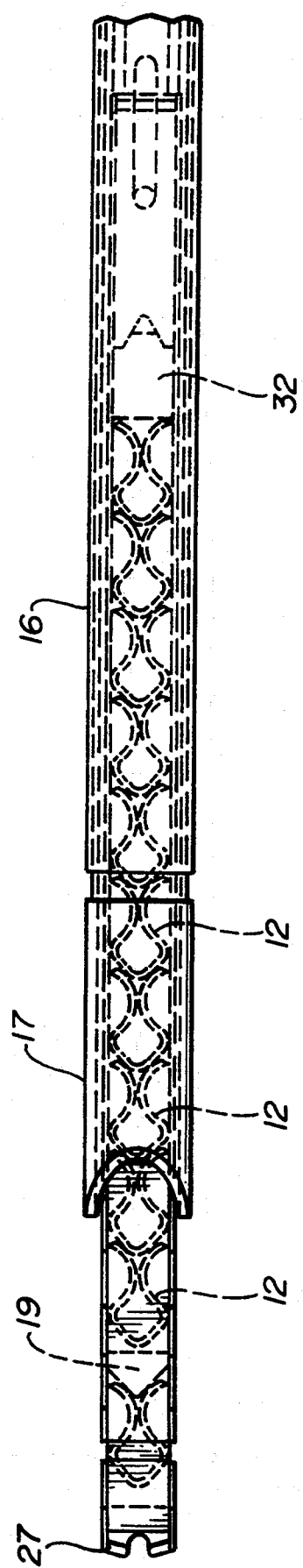

SURGICAL CLIP APPLIER

RELATED APPLICATION

This application claims priority from DE P4317590.2, filed May 24, 1993, and is a continuation-in-part of U.S. Ser. No. 08/059,147, filed May 7, 1993.

BACKGROUND OF THE INVENTION

The invention relates to a clip-applying apparatus for laparoscopic surgical operations, whereby the clips made from a bendable filamentary material, are brought with the help of the apparatus into a closed shape, firmly clamping the tissue located therebetween.

According to known art, clip-applying apparatuses are described which consists of a tube-like system at a distal end of which a clip-holding and clip-shaping mechanism is located, while the other, proximal end displays an actuation mechanism.

The distal end of the clip-applying apparatus is introduced into the patient's abdominal cavity through a cannula and positioned at the vessel to be tied. Through pressure on the actuation mechanism, the shaping of ligature clip, and thus the clamping of the vessel is effected, via the tube-like system.

According to the art, endoscopic apparatuses for the introduction of ligature clips and staples are also known. With such apparatuses, the distal end is of forcipate design for the reception and shaping of the staple. With the actuation mechanism located at the proximal end of the apparatus, the distal end is guided into the application area, the staple is laid around the vessel to be clamped and shaped by means of the forcipate system until the vessel is completely clamped.

The staples used according to the known prior art correspond largely in their shape to the form of office staples. With modern minimally invasive operation techniques, surgical staples are used which are guided by means of a clip-inducing apparatus through a cannula to the operation are in the body. Since, with the apparatuses described, the staples carried along by the induction apparatus are advanced with the rectilinear crown or base side crosswise to the longitudinal axis of the cannula and the cannula customarily used has a limited opening for the guiding through of instruments with a diameter of 5 or 10 mm, limits are also set to the size of the staples. The disadvantage of the described technique is thus that only staples of relatively small basic length (and thus small circumference and small overall size) are usable in endoscopic operations through cannulae.

According to U.S. Ser. No. 08/059,147, a new type of surgical clip, the so-called "omega" clip, was therefore created with is introducible with an induction apparatus through a cannula with pre-set diameter and shapable into a closed shape with a greater circumference than conventional clips. This omega clip is not usable with conventional applier apparatuses.

It is therefore the object of the invention to create a clip or staple applying apparatus which has at its distal end a holding and shaping mechanism for omega clips, which is triggerable via an actuation mechanism located at the proximal end.

SUMMARY OF THE INVENTION

An apparatus which is characterized by the following main features, serves to achieve this object:

The rod system consists of an outer guide tube in which there is arranged an inner sliding sleeve, displaceable coaxially to the outer guide tube, in which are located an elongated support rod fixed relative to the outer guide tube an elongated slide displaceable on the support rod. The holding and shaping mechanism comprised by sliding sleeve, support rod and slide, project from the distal end of the outer guide tube in a manner guaranteeing the holding and shaping function of the clip or staple applying apparatus.

The proximal end of the outer guide tube is firmly connected to the handle of the operating device and the movable actuating lever of the operating device is in active connection with the slide and the sliding sleeve at their proximal ends enabling a joint displacement of the sliding sleeve and of the slide running ahead of the sliding sleeve in the direction of the distal end, designed as an anvil. After the distal end of the slide, designed as a tip, has struck the anvil, it displaces the sliding sleeve in the same direction beyond the distal end of the support rod and of the slide. The sliding sleeve and the slide return to the starting position in the proximal direction upon release of the actuating lever.

DESCRIPTION OF THE DRAWINGS

The invention will now be described in more detail with reference to an embodiment. The associated drawings shown:

FIG. 4 the distal zone apparatus with fitted magazine for several omega clips,

FIG. 5 a plan view of FIG. 4,

DETAILED DESCRIPTION OF THE INVENTION

Figure 1:
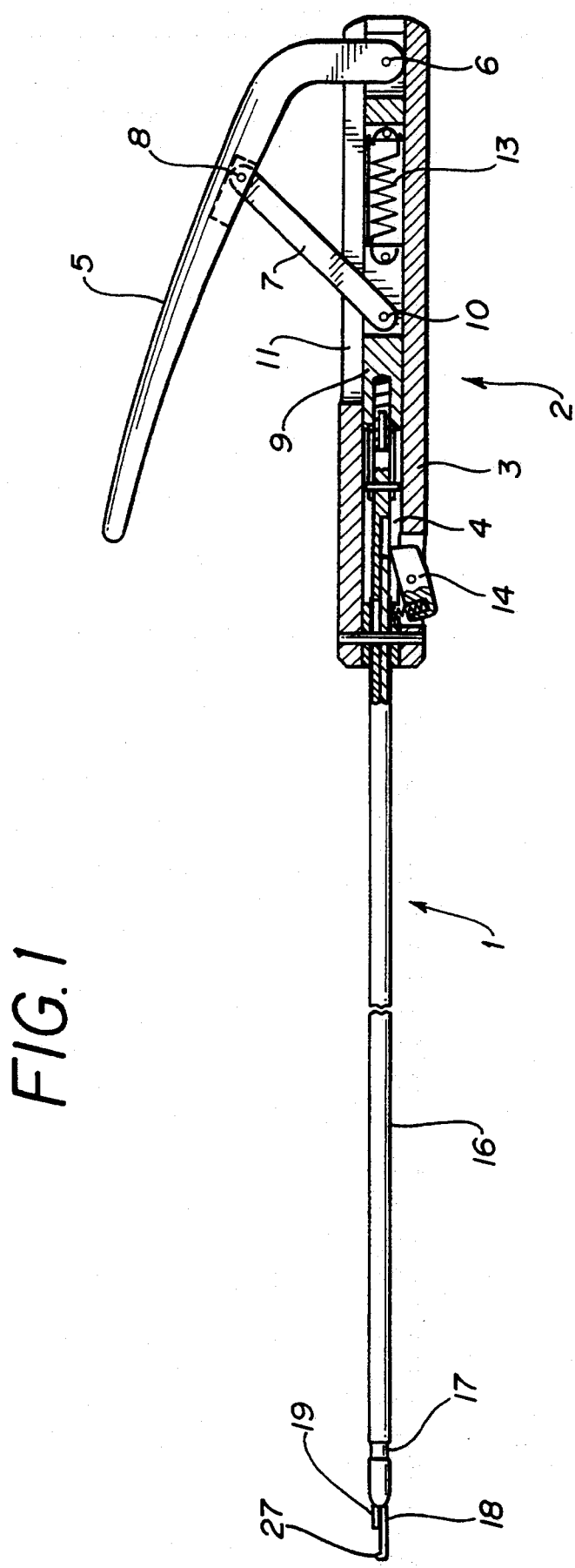
FIG. 1 a side view of the apparatus according to the invention.

The staple or clips applying apparatus represented in its entirety in FIG. 1 consists of an elongated rod system 1. This rod system 1 has several elements which guarantee, via an operating device 2 arranged at the proximal end, the holding and shaping of the omega clip at the distal end.

The operating device 2 consists of a sleeve-shaped handle 3 which has a guide bore 4 running in axial direction. At the end of the handle 3, an angled actuating lever 5 is housed swivellable on one side about a cylindrical pin 6. The free limb of the actuating lever 5 runs above the handle 3 in such a way that both the handle 3 and the actuating lever 5 can be grasped simultaneously by the operator's hand.

The transmission of manual force within the apparatus takes place via a knee-joint mechanism whose member 7 is housed pivotable on one side, in the central zone of the actuating lever 5, about a cylindrical pin 8; and on the other side, in a pressure rod 9 axially displaceable in the guide bore 4 of the handle 3, about a cylindrical pin 10. Member 7 is guided through a longitudinal slot 11 located in the handle 3. This longitudinal slot 11 located in the handle 3 is so designed that it guarantees the movement both of the member 7 and of the actuating lever 5 between defined end-positions, one end-position being determined by the readiness of the apparatus to receive a tissue fastener such as an omega clip or staple 12 and the other end-position by the completed shaping of the omega clip 12.

Accordingly, the clip-holding and the clip-shaping elements are to be moved by the operating device 2.

The actuating lever 5 is held in its starting position by a tension spring 13 acting between the pressure rod 9 and the proximal end of the handle 3, if no manual force is acting on the actuating lever 5. The stops 14 arranged at the handle 3 are not engaged with the clip-holding and clip-shaping elements, the return of the pressure rod 9 being limited by a spacer 15.

This position of the operating device 2 corresponds to the readiness position of the apparatus for receipt of an omega clip 12.

The clip-holding and clip-shaping elements are arranged in an outer guide tube 16 with a length necessary for laparoscopic surgical operations and a diameter permitting guidance through a cannula. This outer guide tube 16 is firmly connected with its proximal end to the handle 3 of the operating device 2, while the other, distal end of the guide tube 16 is open and permits the mergence of the clip-holding and clip-guiding elements.

Arranged coaxial to the outer guide tube 16 is an inner sliding sleeve 17 which accommodates an elongated support rod 18, fixed relative to the handle 3 and the outer guide tube 16, and an elongated slide 19, displaceable on the support rod 18. These clip-holding and clip-shaping elements emerge far enough from the distal end of the outer guide tube 16 to guarantee the clip-holding and clip-shaping function of the apparatus 1.

While the outer guide tube 16 and the support rod 18 are fixed to the handle 3 by a cylindrical pin 20, the sliding sleeve 17 and the slide 19 are in active connection with the pressure rod 9 of the operating device 2. Thus, the sliding sleeve 17 and the slide 19 experience a longitudinal displacement between the described end-positions.

There is a firm connection between the pressure rod 9 and the sliding sleeve 17, e.g. through welding, which guarantees a direct transmission of the longitudinal displacement of the pressure rod 9 onto the sliding sleeve 17. The slide 19, displaceable on the fixed support rod 18, is on the other hand in active connection with the pressure rod 9 via a compression spring 21. To this end, the pressure piece or rod 9 is provided at its distal end with an axial blind bore 22 which accommodates both the proximal end of the sliding sleeve 17 and the proximal end of the slide 19, the compression spring 21 being arranged between the slide 19 and the bore 22.

The necessary relative axial displaceability between the sliding sleeve 17 on the one hand the slide 19 on the other is limited by a cylindrical pin 23, inserted in the slide 19, whose projecting ends are guided in opposing longitudinal holes 24 of a bushing 25, which is firmly connected to the pressure rod 9 and surrounds the sliding sleeve 17. In the area of the oblong holes 24, the sliding sleeve 17 also has corresponding oblong holes 26.

To guarantee the process of the introduction of the omega clip 12, the support rod 18 carries at its distal end a protruding anvil 27 which has an angled bearing surface 28 for the tip of the omega clip 12 laid on the support rod 18. In the situation in which an omega clip 12 is placed by the clip applying apparatus 1, both the slide 19 and the sliding sleeve 17 are in an end-position which corresponds to the actuating lever 5 located in the starting position. The position of the sliding sleeve 17 vis-á-vis the position of the slide 19 is set back relative to the distal end of the clip-applying apparatus. Through pressure on the actuating lever 5, the pressure rod 9 is moved in the direction of the distal end. The pressure rod 9 displaces the sliding sleeve 17 directly and the slide 19 indirectly via the compression spring 21 together in the same direction until the slide 19 presses the omega clip 12 against the bearing surface 28 of the anvil 27. As this pressing takes place against the elastic force of the compression spring 21, a secure holding is assured of the unshaped omega clip 12 at the distal end of the clip-inducing apparatus. The pressure on the actuating lever 5 is interrupted by the operator in this phase in which the described necessary holding force is applied.

The clip-inducing apparatus is guided in this state through the cannula into the application area in the inside of the body and positioned at the surgical object.

Through further pressure on the actuating lever 5 as described in FIGS. 6a–6d, the sliding sleeve 17 and the slide 19 are in turn moved by the pressure rod 9 in the direction of the distal end. The tipped end of the slide 19 slides between the limbs of the omega clip 12 and bends these apart until the feed movement of the slide 19 is ended by the fixed anvil 21. The result of further pressure on the actuating lever 5 is that the slide 17 switches with its proximal end against the elastic force of the compression spring 28 into the bore 22 of the pressure rod 9, while the sliding sleeve 17 is pushed beyond the distal end of the slide 17 and of the support rod 18, and the free limbs of the omega clip 12 are deformed forward into the closed shape.

The different situations of the clip-inducing apparatus can be fixed by means of the stops 14 arranged in the handle 3 through form-locking engagement with the sliding sleeve 17.

Upon release of the actuating lever 5, the pressure rod 9 and thus the actuating lever 5 is guided back into the starting position by the tension spring 13. Through the direct connection between pressure rod 9 and sliding sleeve 17, the sleeve 17 is also guided back directly into the staring position. During this rearward movement the compression spring 21 relaxes and the slide 19 is pulled into the starting position via the cylindrical pin 23 guided in the oblong holes 24 of the bush 25.

The introduced and formed omega clip 12 thus lies free and the apparatus can be removed from the body through the cannula in order to be reloaded if necessary.

Figure 2:
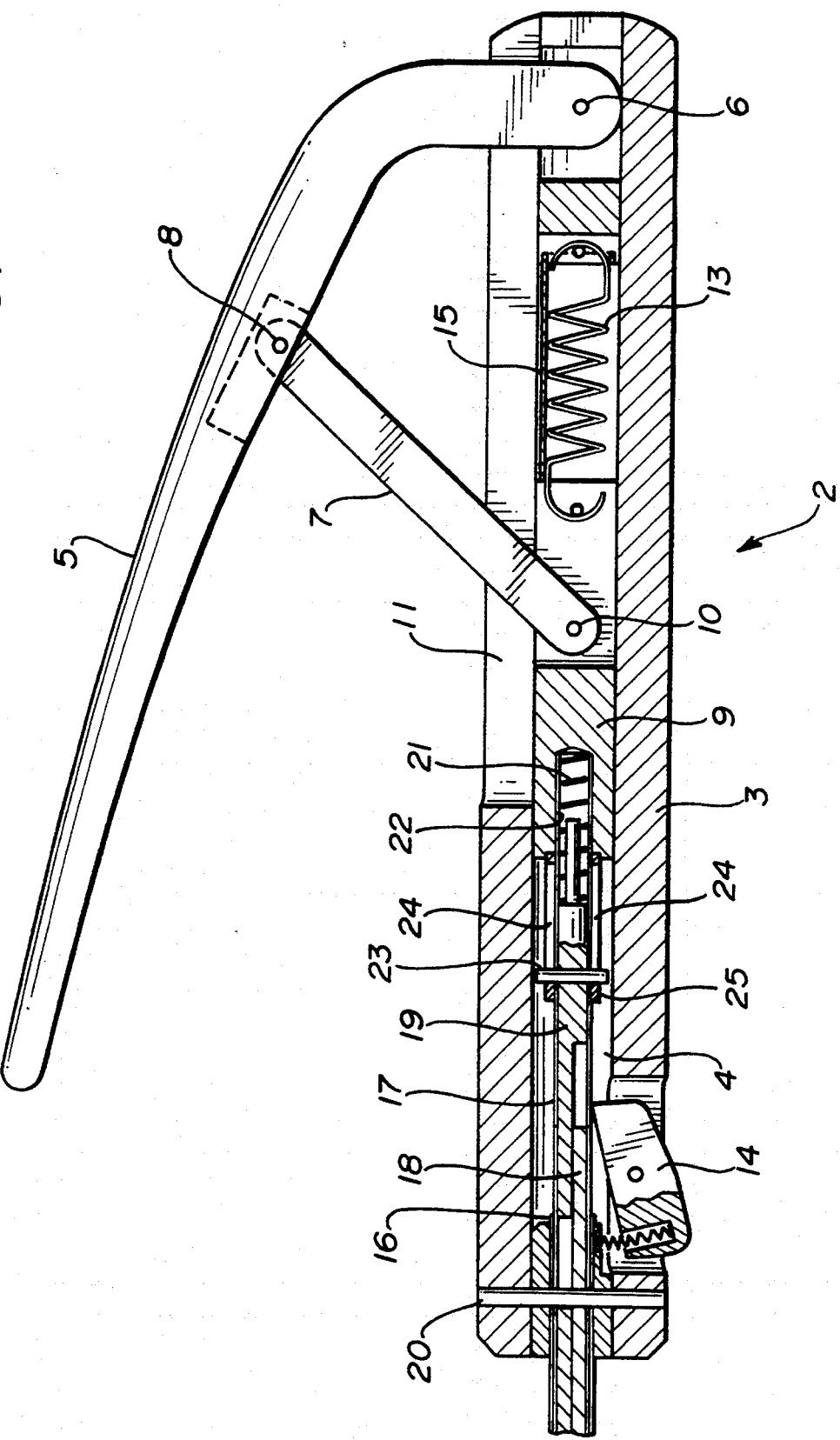
FIG. 2 a sectional representation of the side view of the operating device.
Figure 3:
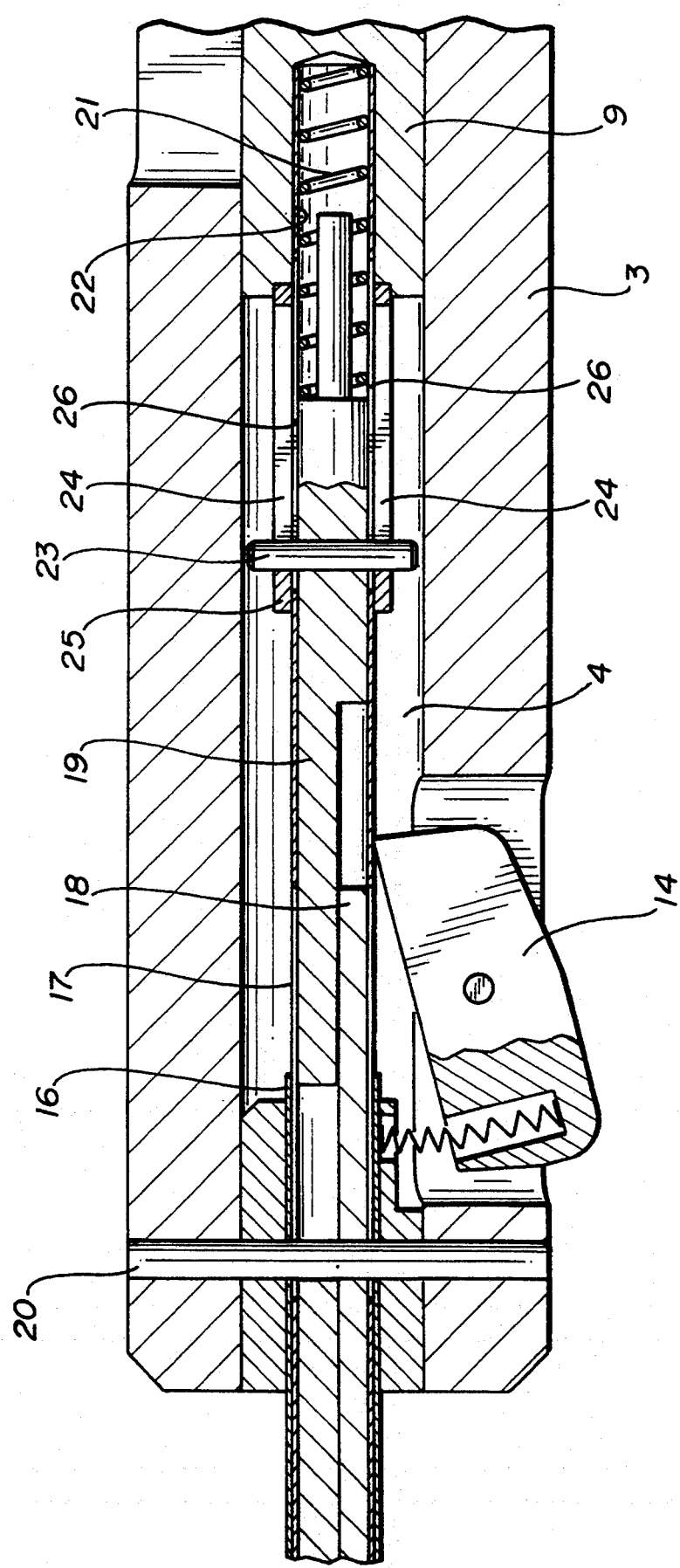
FIG. 3 an enlarged representation of FIG. 2.
Figure 6A:
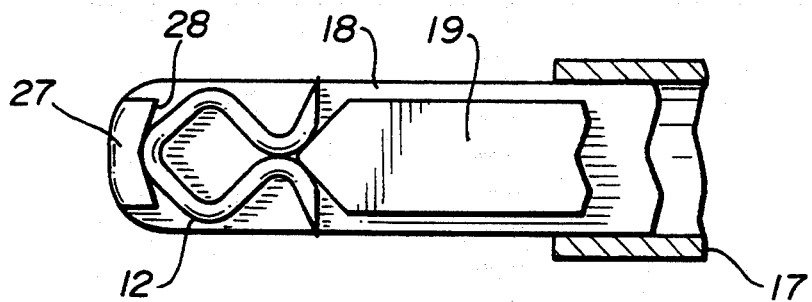
FIG. 6a, 6b, 6c and 6d views of chronologically successive shaping steps during the introduction of a specific type of omega clips, and FIG. 7a, 7b and 7c views of chronologically successive shaping steps during the induction of another type of omega clips.
Figure 6B:
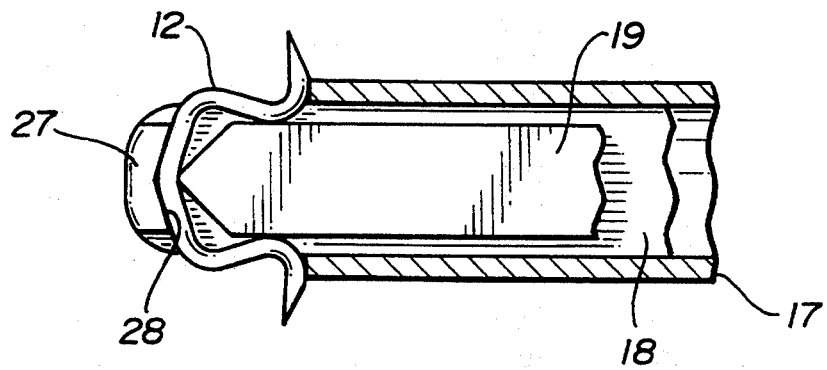
Figure 6C:
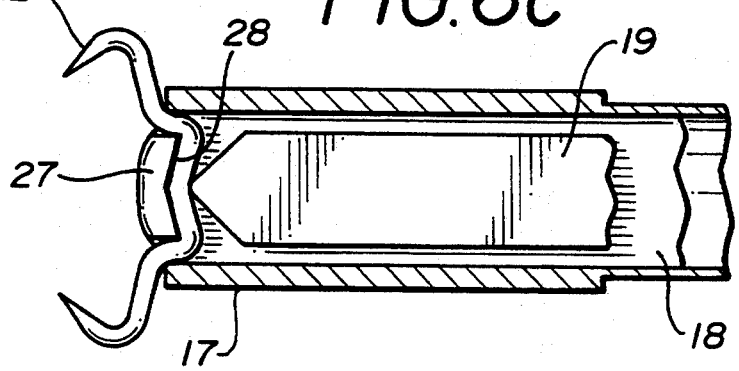
Figure 6D:
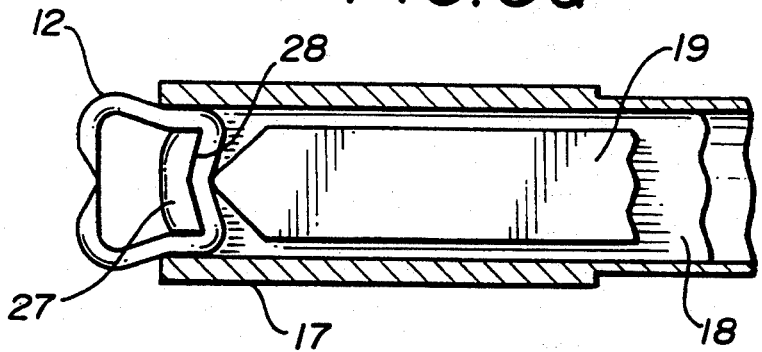
Figure 7A:
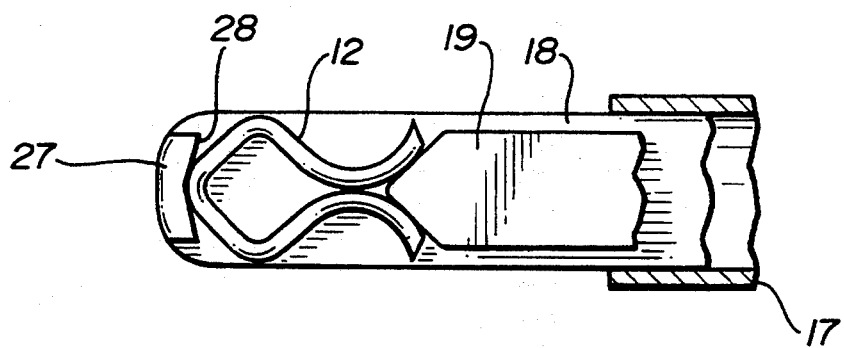
Figure 7B:
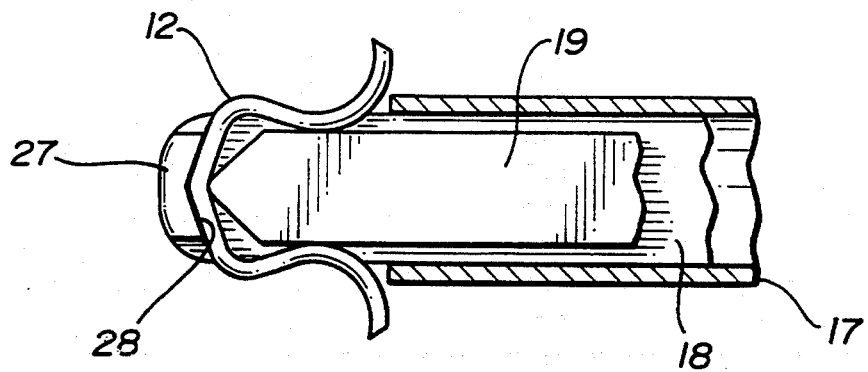
Figure 7C:
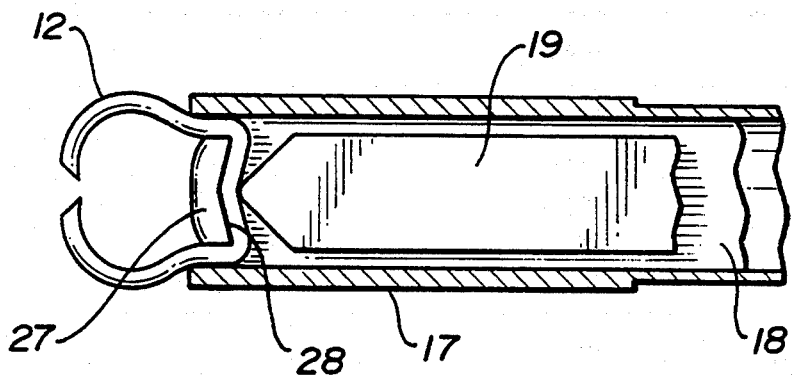

The embodiment described according to FIG. 1–3 assumes a single use of the apparatus according to the invention. This means that the clip-inducing apparatus must be reloaded outside the body after the induction of the omega clip 12. However, since the surgical procedure frequently requires several omega clips 12 to be induced, it is recommended that a stack of omega clips 12 be provided inside the clip-inducing apparatus, from which the clip-holding and clip-inducing mechanism can be loaded in t he vicinity of the surgical object.

FIGS. 4 and 5 show the equipping of the clip-inducing apparatus with a magazine or cartridge 29 which is loaded with several omega clips 12 lying one behind the other.

The magazine 29 is formed of an elongated housing 30 which, inside the sliding sleeve 17, surrounds the support rod 18, the slide 19 and a series of omega clips 12 lying one behind the other on the slide 19. The omega clips 12 are so aligned that the tip of the clip engages between the limbs of the clip in front.

The housing 30 is provided at its distal outlet end with a holding-down device 31 which guarantees that the introduced omega clip 12 does not fall out of the clip-holding and clip-shaping mechanism.

The opposite, proximal and of the housing 30 has a spring-driven stop mechanism 32 with distal movement, which causes feeding of the foremost omega clip 12 into the space, left free by the slide 19 guided back into the starting position, between the anvil 27 and the tip of the slide 19. Through a spring 33, the omega clip 12 is directed into the described space after its forward movement and the withdrawal of the slide 19.

The placement of the foremost omega clip 12 takes place as described for the example according to FIG. 1.

After the stock of preferably ten omega clips 12 has been used the empty magazine 29 can be pulled out of the sliding sleeve 17 in the direction of the distal end of the apparatus 1, filled with new omega clips 12 and re-inserted in the apparatus 1.

What is claimed is:

1. Apparatus consisting of a cylindrical rod with a proximal end holding an actuating device and a distal end containing a holding and shaping mechanism comprising:
    an outer guide tube in which there is arranged an inner sliding sleeve, displaceable coaxially to the outer guide tube;
    an elongated support rod fixed relative to the outer guide tube and an elongated slide having an anvil at its distal end displaceable on the support rod;
    said sliding sleeve and support rod projecting from the distal end of the outer guide tube;
    a movable actuating mechanism contained at the proximal end of the guide tube operatively connected with the slide and the sliding sleeve, in such a way that distal displacement of the sliding sleeve and of the slide causes said slide to strike said anvil;
    wherein said sleeve and said slide are also retractable in the proximal direction upon release of said actuating lever; and
    further comprising a sleeve-shaped handle which has a guide bore running in axial direction therethrough, a trigger being housed in said handle in such a way that both the handle and the trigger can be grasped simultaneously by the operator's hand, the transmission of manual force from said trigger taking place via a pressure rod operatively connected to said trigger and axially displaceable in the guide bore of the handle, said pressure rod being connected at its distal end with said sliding sleeve and said slide.

2. Apparatus according to claim 1, characterized in that a magazine containing several tissue fasteners is arranged in the sliding sleeve, said magazine consisting of an elongated housing which holds said fasteners, a holding-down device for preventing an unintentional falling out of a fastener from same apparatus mechanism; and a spring-driven mechanism which upon distal movement feeds the front most further into the space between the anvil and the tip of the slide.

3. Apparatus according to claim 2, characterized in that the sliding sleeve is directly connected to the pressure rod and the slide is indirectly moved by said pressure rod via coaxially acting compression spring, and further containing limiting means between said sliding sleeve and said slide for limiting the relative displaceability between said sleeve and said slide.

4. Method for introducing omega shaped clips, in particular for laparoscopic operations, by means of an apparatus consisting of a cylindrical rod with a proximal end holding an actuating device and a distal end containing a holding and shaping mechanism comprising:
    an outer guide tube in which there is arranged an inner sliding sleeve, displaceable coaxially to the outer guide tube;
    an elongated support rod fixed relative to the outer guide tube and an elongated slide having an anvil at its distal end displaceable on the support rod;
    said sliding sleeve and support rod projecting from the distal end of the outer guide tube;
    a movable actuating mechanism contained at the proximal end of the guide tube operatively connected with the slide and the sliding sleeve, in such a way that distal displacement of the sliding sleeve and of the slide causes said slide to strike said anvil;
    wherein said sleeve and said slide are also retractable in the proximal direction upon release of said actuating lever;
    said method comprising:
        insertion of an omega shaped clip into the space formed between the anvil and the slide;
        advancing of the sliding sleeve and the slide exertion of pressure on said trigger until the omega clip is fixed between said anvil and said slide;
        positioning said apparatus with an omega clip at its distal end at the surgical site;
        further advancing distally said sliding sleeve and said slide through continued exertion of pressure on said trigger, during which said slide slides between the limbs of said omega shaped clip and bends said limbs open until distal advance of the slide is stopped by the anvil;
        further advancing the said sliding sleeve through continued exertion of pressure on said trigger, the distal end of the sliding sleeve being pushed beyond the distal ends of said support rod and said slide and the limbs of the omega clip being bent forward so as to engage said surgical site; and
        releasing said trigger to cause said sliding sleeve and said slide to move proximally to release said clip and permitting a loading of said apparatus with a subsequent omega clip.

* * * * *